United States Patent [19]

Whisenhunt et al.

[11] Patent Number: 4,731,489

[45] Date of Patent: Mar. 15, 1988

[54] PROCESS FOR PRODUCTION OF GASOLINE BLENDING STOCK

[75] Inventors: David E. Whisenhunt; Gregg L. Byers; Uday S. Hattiangadi, all of Ponca City, Okla.

[73] Assignee: Conoco Inc., Ponca City, Okla.

[21] Appl. No.: 886,850

[22] Filed: Jul. 18, 1986

[51] Int. Cl.$^4$ .............................................. C07C 41/06
[52] U.S. Cl. ..................... 568/697; 568/899
[58] Field of Search ................... 568/697, 899

[56] References Cited

U.S. PATENT DOCUMENTS

| | | | |
|---|---|---|---|
| 3,135,807 | 6/1964 | Grassilli et al. | 260/614 |
| 3,849,082 | 11/1974 | Kozlowski et al. | 44/56 |
| 3,912,463 | 10/1975 | Kozlowski et al. | 44/56 |
| 3,979,461 | 9/1976 | Ancillotti et al. | 260/614 A |
| 4,071,567 | 1/1978 | Ancillotti et al. | 260/614 A |
| 4,148,695 | 4/1979 | Lee et al. | 203/63 |
| 4,161,496 | 7/1979 | Humbert et al. | 585/836 |
| 4,182,913 | 1/1980 | Takezono et al. | 568/697 |
| 4,334,890 | 6/1982 | Kochar et al. | 44/53 |
| 4,423,251 | 12/1983 | Pujado et al. | 568/697 |

Primary Examiner—Howard T. Mars

[57] ABSTRACT

A process for producing a gasoline blending stock of methyl tertiary butyl ether and tertiary butyl alcohol wherein a first catalytic etherification of isobutene and methanol produces methyl tertiary butyl ether and unreacted methanol. The etherification product including isobutene and remaining methanol is reacted with water and fresh isobutene in a second catalytic reaction where both etherification and hydration occur. This essentially exhausts the methanol while the hydration reaction to tertiary butyl alcohol prevents undesired side reactions.

9 Claims, 3 Drawing Figures

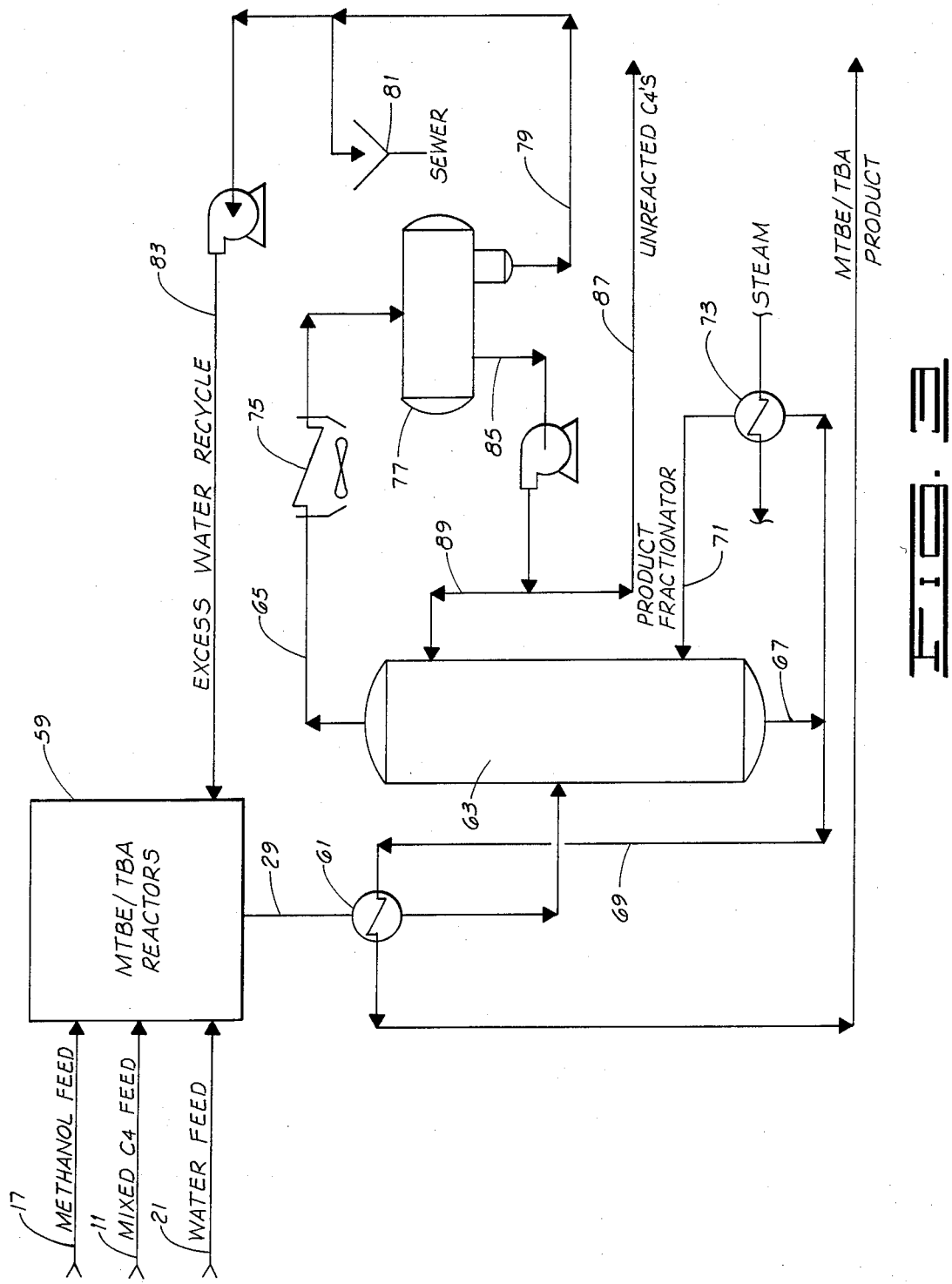

PROCESS FOR PRODUCTION OF GASOLINE BLENDING STOCK

BACKGROUND OF THE INVENTION

1. Field of the Invention

This invention relates in general to processes for producing gasoline octane enhancers, and more particularly, to processes for producing high octane gasoline blending components such as methyl tertiary butyl ether and tertiary butyl alcohol.

2. Brief Description of the Prior Art

In producing gasoline it has recently been desirable to use high octane blending components such as methyl tertiary butyl ether (MTBE) so that new blends of unleaded gasoline can be of sufficiently high octane rating. The typical process for producing MTBE catalytically reacts methanol with isobutene in a mixed $C_4$ stream. The mixed $C_4$ stream with isobutene serves as the feed for this process and is commonly derived from conventional fluid catalytic cracking units and coking operations present in crude oil refineries.

The process for catalytically reacting methanol with isobutene to form MTBE is a well-known process of etherification. In this process a stoichiometric excess of methanol is mixed with isobutene in the presence of an acidic ion exchange-type catalyst such as AMBERLYST-15. AMBERLYST-15 (Rohm and Haas) is a cationic, strongly acidic, ion exchange resin containing a sulfonated polystyrene cross-linked with divinyl benzene. An excess of methanol is used to attain a good conversion of isobutene and to suppress side reactions resulting in dimers, trimers and higher molecular weight polymers of isobutene. These products are of lower octane and reduce the desirability of the product.

A problem with all present etherifiction processes for producing MTBE is that the excess methanol needed to suppress production of less desirable products is itself a troublesome component of the reaction product. The excess methanol remains with the unreacted $C_4$'s after MTBE separation and must be removed from the unreacted $C_4$'s before further processing, for example, alkylation. The separated methanol is recycled to etherification or can be used elsewhere. This methanol separation and recovery typically requires a water wash tower, a methanol stripper, and corresponding pumps and heat exchangers. This separation is, therefore, undesirably expensive.

In some instances it is desirable to convert the isobutene to MTBE by etherification and to tertiary butyl alcohol (TBA) by hydration. Since TBA is a relatively high octane blending compound, the combined TBA and MTBE is a desirable gasoline blending stock. TBA can also be separated and used for other purposes. U.S. Pat. No. 4,423,251 shows a process for converting isobutene to both TBA and MTBE. More particularly, it shows an isobutene stream which is divided into two portions, the first of which is reacted for hydration to TBA. The second portion of the isobutene and remaining isobutene from the hydration process are introduced into an etherification zone. In this zone excess methanol is used to obtain a good conversion of the isobutene to the MTBE. Thus, the problem of separating excess methanol is present in this process in the same manner as other etherification processes.

It is therefore an object of the present invention to provide an improved process for producing a gasoline blending stock from isobutene. It is also an object of the present invention to provide such a process that produces a high octane combination of MTBE and TBA from isobutene and which is simpler and less expensive than previous processes. It is still further an object of the present invention to provide such a process which does not require separation of methanol following etherification.

SUMMARY OF THE INVENTION

In accordance with the above objects, the present invention provides a process for producing gasoline blending components from a $C_4$ mixture including isobutene. The process includes reacting for etherification in a first catalytic reaction zone methanol and a $C_4$ mixture including isobutene, the isobutene being present in a substoichiometric quantity to the methanol. This reaction produces an etherification product comprising methyl tertiary butyl ether, a small amount of unreacted isobutene and unreacted methanol. Unreacted $C_4$ compounds also remain in the etherification product. The etherification product, water and additional $C_4$ mixture including isobutene is reacted for hydration and etherification in a second reaction zone. The reaction for hydration and etherification produces tertiary butyl alcohol, methyl tertiary butyl ether and a sufficiently low quantity of methanol so that separation of methanol from the reaction product is not necessary.

The amount of water fed to the second reaction zone is in excess of the amount required to react stoichiometrically with the isobutene remaining in the etherification product and the additional $C_4$ mixture which brings about conversion of isobutene to tertiary butyl alcohol. The total overall amount of methanol utilized in the process is controlled at a level whereby a substoichiometric ratio of methanol to isobutene results. This permits essentially total conversion of the methanol. In addition, since isobutene is present in excess of methanol in the second reaction zone, additional methyl tertiary butyl ether is formed whereby essentially all of the methanol is reacted. The reaction product, therefore, from the second reaction zone contains essentially no methanol. This eliminates the need for methanol separation devices and steps which are required by the prior art.

The process of reaction in the first and second reaction zones is preferably a catalytic reaction using an acidic ion exchange resin-type catalyst such as AMBERLYST-15. Since the same catalyst is used in both zones, etherification can also proceed in the second zone where the main reaction is hydration.

Preferably the overall amount of methanol utilized in the process is in the range of from about 0.3 to about 0.99 times the amount required for the stoichiometric reaction with isobutene fed to the process. The amount of water utilized is in the range of from 1 to 2.5 times the amount required for stoichiometric reaction with isobutene in the second reaction zone. The ratio of the amounts of isobutene introduced to the first reaction zone relative to the second reaction zone is adjusted to produce a desired ratio of MTBE to TBA in the gasoline blending stock product which results.

For a further understanding of the invention and further objects, features and advantages thereof, reference may now be had to the following description taken in conjunction with the accompanying drawings.

BRIEF DESCRIPTION OF THE DRAWINGS

FIG. 3 is a schematic view of the process of the present invention including the portions shown in FIGS. 1 and 2.

DESCRIPTION OF THE PREFERRED EMBODIMENT

The feed stock of the present invention is a mixture of $C_4$ hydrocarbons of the type commonly obtained from petroleum refineries. For example, fluid catalytic cracking units and coking operations often result in a mixture of $C_4$ hydrocarbons including isobutene, isobutane, normal butane, butene-1 and butene-2. A typical mixture would contain at least 90% $C_4$'s and approximately 10% or more of isobutene.

The first step in the process of the present invention is etherification in a catalytic reaction zone. In this zone, the isobutene will be converted by reaction with an alcohol to form an ether. The most preferred alcohol is methanol and the most preferred product is methyl tertiary butyl ether (MTBE). The preferred catalyst for the first reaction zone is an acidic ion exchange resin-type catalyst such as AMBERLYST-15.

The second step of the present invention comprises a hydration and etherification reaction in a second catalytic reaction zone to produce both methyl tertiary butyl ether and tertiary butyl alcohol. Isobutene reacts with water in this reaction zone for hydration adn any methanol reacts with the isobutene for etherification. As with the first reaction zone the preferred catalyst is an acidic ion exchange resin-type catalyst such as AMBERLYST-15. The main concept of the present invention is to create a high octane gasoline blending stock of MTBE and TBA without resulting in an excess of methanol. This is achieved by using an overall substoichiometric ratio of methanol to isobutene and by combining etherification and hydration so as to prevent undesirable side reactions which would otherwise occur in a substoichiometric methanol etherification.

Figure 1:
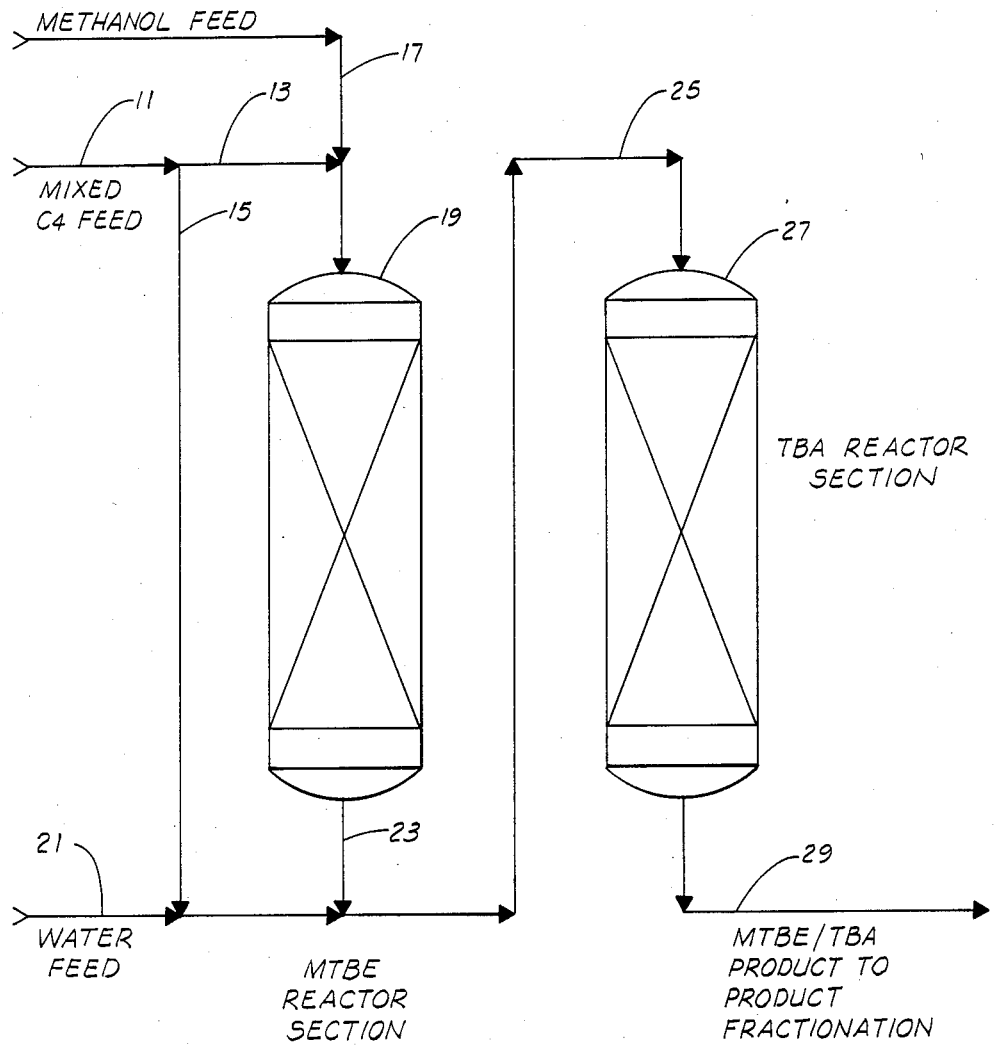
FIG. 1 is a schematic view of a portion of the process of the present invention.

Referring now to FIG. 1, a mixed $C_4$ feed stock stream is shown at 11. This mixed $C_4$ feed stock stream 11 is separated into streams 13 and 15. The first of the divided streams, stream 13, is mixed with a methanol feed stream 17 and the combination of these two streams is introduced to a MTBE reactor section 19.

The MTBE reactor section 19 is a conventional fixed-bed catalytic reactor containing an acidic ion exchange resin-type catalyst such as AMBERLYST-15. In the reactor section 19 isobutene in the feed reacts with methanol in the presence of the catalyst to form MTBE. The mechanism of this reaction and the reactor section 19 are conventional and well-known in the art.

The second portion of the mixed $C_4$ stream, stream 15, is mixed with a water feed stream 21. It is also mixed with the etherification product stream 23 which exits the MTBE reactor section 19 comprised of MTBE, unreacted isobutene, unreacted methanol and other $C_4$'s. That is, the product stream 23 from the reactor section 19 is mixed with the isobutene and mixed $C_4$'s in stream 15 and a water feed from stream 21. Together these streams form a stream 25 which is introduced into a TBA reactor section 27.

The TBA reactor section 27 is a fixed bed catalytic reactor containing an acidic ion exchange resin-type catalyst such as AMBERLYST-15. Thus, the same catalyst as present in the reactor 19 is present in the reactor 27.

The catalytic reaction in the reactor 27 is mainly a hydration reaction but etherification occurs as well. The hydration reaction reacts water and isobutene to form TBA. The amount of feed water supplied to the reactor section 27 is in excess of the amount required to react stoichiometrically with the isobutene in the reactor 27. In this manner, most of the isobutene will be converted to TBA in the reactor. In addition, since isobutene is now greatly in excess of methanol, more MTBE will be formed and any remaining methanol will be reduced almost to extinction. Since an abundance of water is available to form TBA, the undesired side reactions such as dimerization of isobutene is suppressed.

Very important to the present invention and contrary to the prior art, the overall amount of methanol in stream 17 is substoichiometric to the amount of isobutene in the stream 11 with respect to the methanol/isobutene catalytic reaction to form MTBE. The ratio of methanol to isobutene in the reactor section 19 is in excess of a stoichiometric ratio so that all but a small amount of the isobutene is converted to MTBE and undesirable side reactions do not take place. While a substoichiometric amount of methanol with respect to isobutene exists in the reactor section 27, the presence of water therein and the conversion of isobutene to TBA prevent undesirable side reactions from taking place therein.

The preferred overall range of methanol to isobutene ratio is from 0.3 to 0.99 times the stoichiometric ratio. The most preferred is approximately 0.75 times the stoichiometric ratio.

The preferred water to isobutene ratio in the TBA reactor section 27 is in the range of from 1 to 2.5 times the stoichiometric ratio. This amount of water is sufficient to convert most of the isobutene to TBA and to essentially prevent undesired side reactions.

Exiting the reactor 27 is an MTBE/TBA product which contains very little, if any, methanol. The amount of methanol is sufficiently low so that separation of methanol from the reaction product is not necessary or required as in previous processes. The reaction product stream 29 contains water and unreacted $C_4$'s. The unreacted $C_4$ product can be separated and is substantially free of oxygenated compounds, and hence suitable to be fed directly to an alkylation unit following separation.

Figure 2:
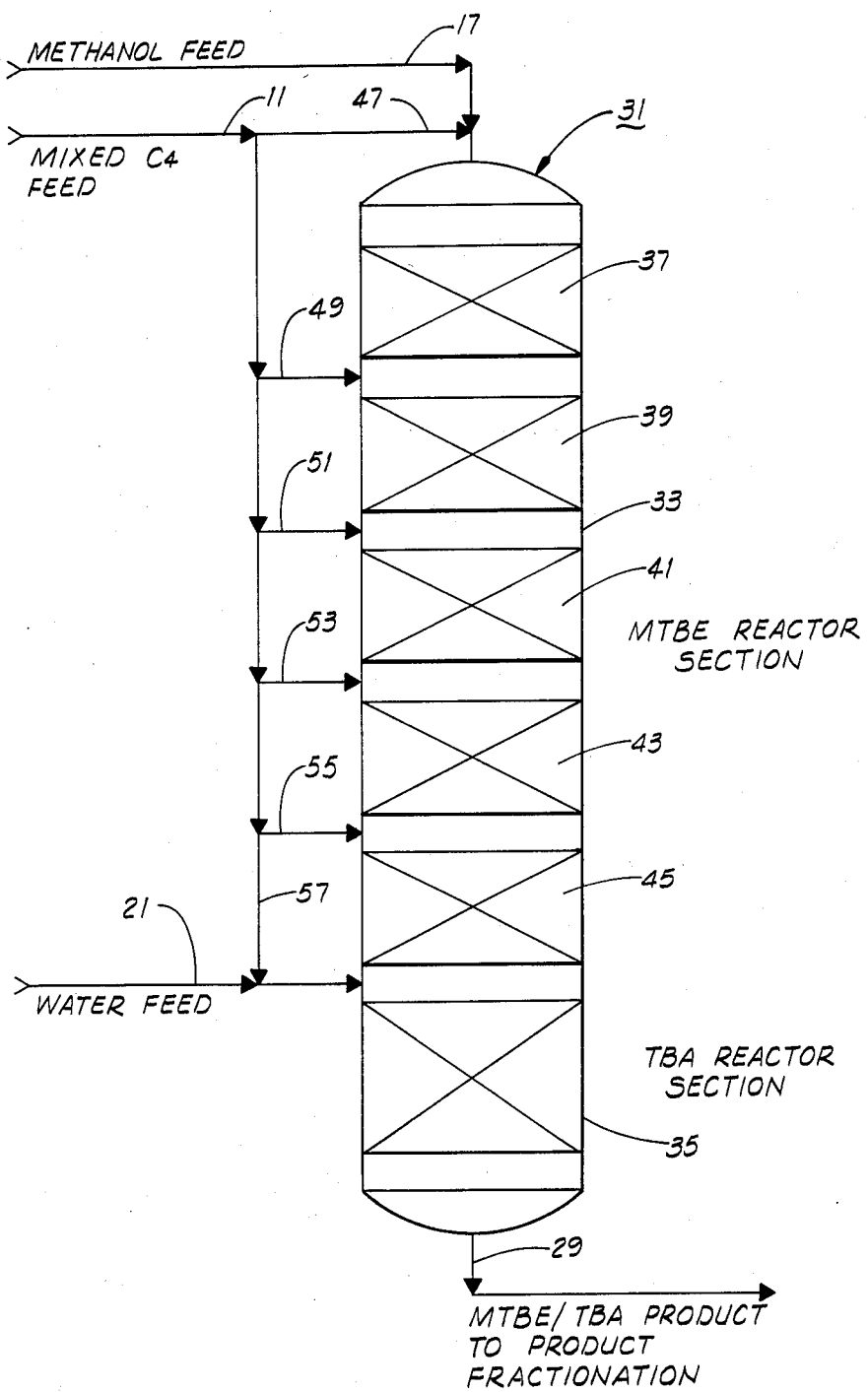
FIG. 2 is a schematic view of an alternate embodiment of a portion of the process of the present invention.

Referring also to FIG. 2, an alternate embodiment of reacting the methanol feed stream 17, the mixed $C_4$ stream 11 and the water feed stream 21 is schematically illustrated. In this embodiment a single reactor 31 includes an upper MTBE reactor section 33 and a lower TBA reactor section 35. The upper MTBE reactor section 33 includes fixed beds 37, 39, 41, 43 and 45 of AMBERLYST-15 catalyst. The reactor 31 also has a multiple feed so that each of the fixed beds 37–45 can have fresh mixed $C_4$ feed introduced to it.

The mixed $C_4$ stream 11 shown in FIG. 2 is divided into streams 47, 49, 51, 53, 55 and 57. Stream 47 is mixed with methanol feed stream 17 and introduced to the reactor 31 and the fixed bed 37. Etherification occurs in the fixed bed 37 and the product moves downwardly in the reactor to fixed bed 39. Stream 49 is introduced to the fixed bed 39 together with the etherification product from the fixed bed 37. This continues in series for each of the etherification fixed beds 37–45 with a fresh C$_4$ feed stream being added at each stage.

By using a multi-stage, multi-feed MTBE reactor section 33, a ratio of methanol to isobutene slightly in excess of stoichiometric can be obtained for the MTBE reactor as a whole while the initial ratio of methanol to isobutene can be greatly in excess of stoichiometric. As with the reactor described with respect to FIG. 1, side reactions such as dimerization of isobutene are suppressed. By utilizing the multi-stage, multi-feed reactor shown in FIG. 2, the methanol to isobutene ratio is near stoichiometric only in the lower beds of the etherification zone so that the side reactions are further suppressed as compared to the single feed reactor section 19 shown in FIG. 1.

The TBA reactor section 35 of the reactor 31 is below the lowest fixed bed etherification reactor section 45. Thus, the etherification product from the entire MTBE reactor section 33 is introduced to the TBA reactor section 35. The water feed stream 21 is mixed with the remaining fresh C$_4$ feed stream 57 and introduced to the TBA reactor section 35. Thus, as with the TBA reactor 27 shown in FIG. 1, the TBA reactor 35 in FIG. 2 receives and reacts the remaining isobutene from the MTBE section and the remaining isobutene in the mixed C$_4$ feed for both etherification and hydration. The etherification and hydration are the same as those described with respect to the etherification and hydration as described for the reactor 27.

As can be seen, the mixed C$_4$ streams 47–55 introduce isobutene to the etherification section 33. Critical to the concept of the present invention is that the combination of these streams and the methanol stream 17 must produce a ratio of methanol to isobutene in excess of a stoichiometric ratio while the overall methanol to isobutene ratio entering the reactor 31 via streams 11 and 17 is a substoichiometric ratio. Preferably, the ratio of methanol to isobutene resulting from the streams 17 and the combination of streams 47–55 is in the range of approximately 0.3 to 0.99 times the stoichiometric ratio, and most preferably approximately 0.75 times the stoichiometric ratio. The division among the streams 47–55 can be adjusted to vary the amount of methanol which enters each etherification section and to maximize the amount of MTBE product while minimizing the undesirable side reactions such as dimerization of isobutene.

Exiting the reactor 31 is an MTBE/TBA product stream 29 containing a relatively small amount of methanol whereby methanol separation is not required prior to product separation.

Referring now to FIG. 3, the product separation downstream of the MTBE/TBA reactors is shown schematically. In FIG. 3, the MTBE/TBA reactors 59 represent either the single reactor 31 of FIG. 2 or the double reactors 19 and 27 of FIG. 1. As stated, the product stream 29 exits the MTBE/TBA reactors 59 and includes MTBE, unreacted C$_4$'s, unreacted water, and negligible methanol.

The product stream 29 exchanges heat in a heat exchanger 61 to heat the stream 29 for product fractionation in a product fractionator 63. The overheads from the stream 65 from the product fractionator will include all of the unreacted C$_4$'s and water. The bottoms from stream 67 from the product fractionator 63 is the MTBE/TBA gasoline additive. This MTBE/TBA gasoline additive product from stream 67 can be removed from the process by means of a product stream 69. Product stream 69 is passed for heat exchange through heat exchanger 61 prior to leaving the system. The remaining portion of stream 67 is recycled for reflux to the product fractionator 63 by means of a stream 71. Stream 71 is heated by means of a heat exchanger 73.

The unreacted C$_4$'s and water stream 65 from the overhead of product fractionator 63 are cooled by an air cooler 75 and introduced to a condenser-separator 77 where the unreacted C$_4$'s are separated from the water. Water is removed from the condenser-separator 77 in a stream 79. Stream 79 can be directed to the sewer 81 or pumped to a recycle stream 83 back to the MTBE/TBA reactors 59.

Unreacted C$_4$'s from the condenser-separator 77 form a stream 85. A portion of these unreacted C$_4$'s are pumped to an unreacted C$_4$'s product stream 87 and the remainder is conveyed for reflux to the product fractionator 63 by means of a stream 89.

The unreacted C$_4$'s stream 87 is substantially free of oxygenated compounds and hence is suitable to be fed directly to an alkylation unit. Thus, no devices for separation of methanol are required, substantially reducing the cost of the equipment and the process.

As can be seen by the above description, the process of the present invention is well adapted to achieve the objects and advantages mentioned as well as those inherent therein. While presently preferred embodiments of the present invention have been described for the purpose of this disclosure, numerous changes can be made by those skilled in the art, which changes are encompassed within the spirit of this invention as defined by the appended claims.

What is claimed is:

1. A process for producing a gasoline blending stock comprising the steps of:
   (a) reacting for etherification in a first catalytic reaction zone methanol and a C$_4$ mixture including isobutene, said methanol being in excess of stoichiometric with respect to said isobutene in step (a) but substoichiometric with respect to the combined isobutene in steps (a) and (b), to produce an etherification product comprising methyl tertiary butyl ether and unreacted methanol; and
   (b) reacting for hydration and etherification in a second reaction zone, water, additional C$_4$ mixture including isobutene, and said etherification product including methanol, whereby an overall reaction product is produced comprising methyl tertiary butyl ether, tertiary butyl alcohol, and essentially no methanol.

2. The process of claim 1 wherein said first and second catalytic reaction zones contain an acidic ion exchange resin-type catalyst.

3. The process of claim 1 wherein the overall ratio of methanol to isobutene is in the range of about 0.3 to about 0.99 times the stoichiometric ratio.

4. The process of claim 3 wherein the overall ratio of methanol to isobutene is approximately 0.75 times the stoichiometric ratio.

5. The process of claim 1 wherein the ratio of water to isobutene in said second reaction zone is in the range of about 1 to about 2.5 times the stoichiometric ratio for forming tertiary butyl alcohol.

6. A process for producing a gasoline blending stock comprising the steps of:
   (a) reacting for etherification in a first multizone catalytic reactor section having a fixed bed of an acidic ion exchange resin-type catalyst in each zone methanol and a C$_4$ mixture including isobutene, said methanol being present in excess of stoichiometric with respect to said isobutene, and a portion of said C$_4$ mixture being added as fresh feed to each zone of said multizone catalytic reactor section, whereby an etherification product comprising methyl tertiary butyl ether and unreacted methanol is produced; and (b) reacting for hydration and etherification in a second reactor section containing a fixed bed of an acidic ion exchange resin-type catalyst said etherification product, water, and additional C$_4$ mixture including additional isobutene, the overall ratio of methanol to the combined isobutene of steps (a) and (b) being substoichiometric, whereby an overall reaction product is produced comprising methyl tertiary butyl ether, tertiary butyl alcohol, and essentially no methanol.

7. The process of claim 6 wherein the overall ratio of methanol to isobutene is in the range of about 0.3 to about 0.99 times the stoichiometric ratio.

8. The process of claim 7 wherein the overall ratio of methanol to isobutene is approximately 0.75 times the stoichiometric ratio.

9. The process of claim 8 wherein the ratio of water to isobutene in said second reaction zone is in the range of about 1 to about 2.5 times the stoichiometric ratio for forming tertiary butyl alcohol.

* * * * *